US006413656B1

United States Patent
Thompson et al.

(10) Patent No.: US 6,413,656 B1
(45) Date of Patent: Jul. 2, 2002

(54) REDUCED SYMMETRY PORPHYRIN MOLECULES FOR PRODUCING ENHANCED LUMINOSITY FROM PHOSPHORESCENT ORGANIC LIGHT EMITTING DEVICES

(75) Inventors: Mark E. Thompson, Anaheim, CA (US); Raymond C. Kwong, Hong Kong (HK)

(73) Assignee: The University of Southern California, Los Angeles, CA (US)

( * ) Notice: Subject to any disclaimer, the term of this patent is extended or adjusted under 35 U.S.C. 154(b) by 0 days.

(21) Appl. No.: 09/152,960

(22) Filed: Sep. 14, 1998

(51) Int. Cl.[7] ............................................... H05B 33/14
(52) U.S. Cl. ....................... 428/690; 428/917; 313/504; 313/506; 427/66
(58) Field of Search ................................. 428/690, 917; 313/503, 504, 506; 427/66

(56) References Cited

U.S. PATENT DOCUMENTS

| 5,203,974 A |   | 4/1993  | Kokako et al. |       |
|-------------|---|---------|---------------|-------|
| 5,294,810 A | * | 3/1994  | Egusa et al. .................. | 257/40 |
| 5,457,565 A |   | 10/1995 | Namiki et al. |       |
| 5,554,220 A |   | 9/1996  | Forrest et al. |       |
| 5,703,436 A |   | 12/1997 | Forrest et al. .............. | 313/506 |
| 5,707,745 A |   | 1/1998  | Forrest et al. .............. | 428/432 |

FOREIGN PATENT DOCUMENTS

EP           0 704 915           4/1996

OTHER PUBLICATIONS

Satoshi Hoshino et al., "Electroluminescence from triplet excited states of Benzophenone", Appl. Phys. Lett. 69 (2), Jul. 8, 1996, pp. 224–226.*

Whitlock et al., "Investigations of Materials and Device Structures for Organic Semiconductor Solar Cells", Optical Eng., vol. 32., No. 8, 1921–1934 (Aug. 1993).

Y. Kunugi, et al., "A Vapochromic LED", *J. Am. Chem. Soc.*, vol. 120, No. 3, pp. 589–590, 1998. (No Month).

C.W. Tang, et al., *Appl. Phys. Lett*, pp. 913–915 (Sep. 21,1987).

S.R. Forrest, et al. *Laser Focus World*, (Feb. 1995), pp. 99–107.

V. Bulovic, et al., 380 *Nature*, 29 (Mar. 1996).

C.W. Tang, et al., "Electroluminescence of doped organic thin films", 65 *J. Appl. Phys.*, pp. 3610–3616 (May 1, 1989).

22 *Aust. J. Chem.*, 229–249 (1969). (No Month)

* cited by examiner

*Primary Examiner*—Marie Yamnitzky
(74) *Attorney, Agent, or Firm*—Kenyon & Kenyon

(57) ABSTRACT

Organic light emitting devices which are comprised of a heterostructure for producing electroluminescence wherein the heterostructure is comprised of an emissive layer containing a phosphorescent dopant compound which has reduced symmetry for producing a saturated red emission with greater brightness. For example, the phosphorescent dopant compound may be comprised of a compound having the structure with formula (II):

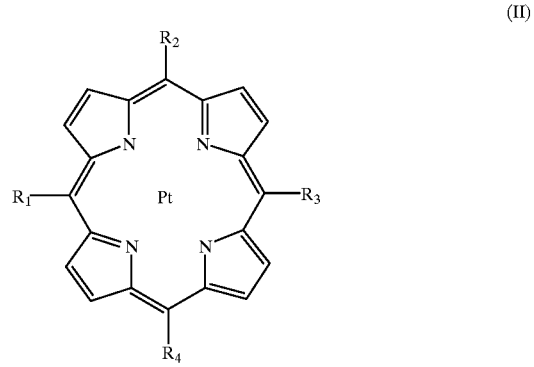

where the R-groups $R_1$, $R_2$, $R_3$ and $R_4$ are, independently of one another, alkyl, aryl or hydrogen, with the proviso that at least one of the R-groups is different from at least one other R-group.

18 Claims, 5 Drawing Sheets

REDUCED SYMMETRY PORPHYRIN MOLECULES FOR PRODUCING ENHANCED LUMINOSITY FROM PHOSPHORESCENT ORGANIC LIGHT EMITTING DEVICES

GOVERNMENT RIGHTS

This invention was made with Government support under Contract No. F33615-94-1-1414 awarded by DARPA. The government has certain rights in this invention.

FIELD OF INVENTION

The present invention is directed to organic light emitting devices (OLEDs) comprised of emissive layers that contain phosphorescent dopant porphyrin molecules having reduced symmetry for producing a saturated red emission with greater brightness.

BACKGROUND OF THE INVENTION

Organic light emitting devices (OLEDs) are comprised of several organic layers in which one of the layers is comprised of an organic material that can be made to electroluminesce by applying a voltage across the device, C. W. Tang et al., *Appl. Pys. Lett* 51, 913 (1987). Certain OLEDs have been shown to have sufficient brightness, range of color and operating lifetimes for use as a practical alternative technology to LCD-based full color flat-panel displays (S. R. Forrest, P. E. Burrows and M. E. Thompson, Laser Focus World, February 1995). Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor, U.S. Pat. No. 5,707,745. This patent disclosed a stacked OLED (SOLED) for which both intensity and color could be independently varied and controlled with external power supplies in a color tunable display device. Each layer in the integrated SOLED was independently addressable and emitted its own characteristic color. This colored emission could be transmitted through the adjacently stacked, transparent, independently addressable, organic layer or layers, the transparent contacts and the glass substrate, thus allowing the device to emit any color that could be produced by varying the relative output of the color-emitting layers. U.S. Pat. No. 5,707,745, thus, illustrates a principle for achieving integrated, full color pixels that provide high image resolution, which is made possible by the compact pixel size. Furthermore, relatively low cost fabrication techniques, as compared with prior art methods, may be utilized for making such devices.

A transparent OLED (TOLED), V. Bulovic, G. Gu, P. E. Burrows, M. E. Thompson, and S. R. Forrest, *Nature* 380, 29 (1996), which represents a further significant step toward realizing high resolution, independently addressable stacked R-G-B pixels, was reported in U.S. Pat. No. 5,703,436, in which the TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg-Ag-ITO electrode layer for electron-injection. A device was disclosed in which the ITO side of the Mg-Ag-ITO electrode layer was used as a hole-injecting contact for a second, different color-emitting OLED stacked on top of the TOLED.

Such devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers separating the anode and cathode of the device. The material of one of these layers is specifically chosen based on the material's ability to transport holes, a "hole transporting layer" (HTL), and the material of the other layer is specifically selected according to its ability to transport electrons, an "electron transporting layer" (ETL). With such a construction, the device can be viewed as a diode with a forward bias when the potential applied to the anode is higher than the potential applied to the cathode. Under these bias conditions, the anode injects holes (positive charge carriers) into the hole transporting layer, while the cathode injects electrons into the electron transporting layer. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. Recombination of this short-lived state may be visualized as an electron dropping from its conduction potential to a valence band, with relaxation occurring, under certain conditions, preferentially via a photoemissive mechanism. Under this view of the mechanism of operation of typical thin-layer organic devices, the electroluminescent layer comprises a luminescence zone receiving mobile charge carriers (electrons and holes) from each electrode.

The materials that function as the electron transporting layer or as the hole transporting layer of the OLED are frequently the same materials that are incorporated into the OLED to produce the electroluminescent emission. Such devices in which the electron transporting layer or the hole transporting layer functions as the emissive layer are referred to as having a "single heterostructure" (SH). Alternatively, the electroluminescent material may be present in a separate emissive layer between the hole transporting layer and the electron transporting layer in what is referred to as a "double heterostructure" (DH).

In addition to emissive materials that are present as the predominant component in the charge carrier layer, that is, either in the hole transporting layer or in the electron transporting layer, and that function both as the charge carrier material as well as the emissive material, the emissive material may be present in relatively low concentrations as a dopant in the charge carrier layer. Whenever a dopant is present, the predominant material in the charge carrier layer may be referred to as a host compound or as a receiving compound. Materials that are present as host and dopant are selected so as to have a high level of energy transfer from the host to the dopant material. In addition, these materials need to be capable of producing acceptable electrical properties for the OLED. Furthermore, such host and dopant materials are preferably capable of being incorporated into the OLED using starting materials that can be readily incorporated into the OLED by using convenient fabrication techniques, in particular, by using vacuum-deposition techniques.

It is desirable for OLEDs to be fabricated using materials that provide electroluminescent emission in a relatively narrow band centered near selected spectral regions, which correspond to one of the three primary colors, red, green and blue so that they may be used as a colored layer in an OLED or SOLED. It is also desirable that such compounds be capable of being readily deposited as a thin layer using vacuum deposition techniques so that they may be readily incorporated into an OLED that is prepared entirely from vacuum-deposited organic materials.

U.S. Ser. No. 08/774,087, now U.S. Pat. No. 6,048,630, which is incorporated herein in its entirety by reference, is directed to OLEDs containing emitting compounds that produce a saturated red emission. The emission layer is comprised of an emitting compound having a chemical structure represented by Formula I:

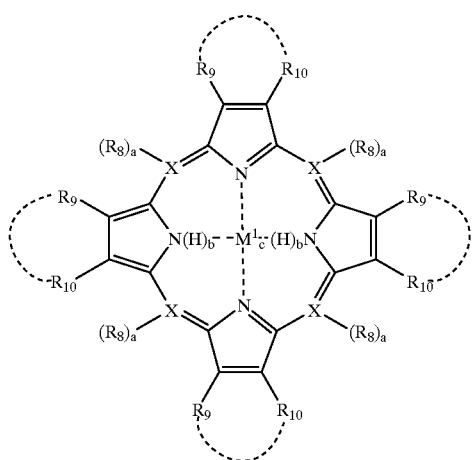

I wherein
  X is C or N;
  $R_8$, $R_9$ and $R_{10}$ are each independently selected from the group consisting of hydrogen, alkyl, substituted alkyl, aryl and substituted aryl; wherein $R_9$ and $R_{10}$ may be combined together to form a fused ring;
  $M_1$ is a divalent, trivalent or tetravalent metal; and
  a, b and c are each 0 or 1;
  wherein, when X is C, then a is 1; when X is N, then a is 0;
  when c is 1, then b is 0; and when b is 1, c is 0.

The examples disclosed in co-pending U.S. Ser. No. 08/774,087, now U.S. Pat. No. 6,048,630, which is incorporated herein in its entirety by reference, included an emissive compound of formula I wherein X=C; $R_8$=phenyl; $R_9$=$R_{10}$=H; c=0; and b=1. This compound has the chemical name 5,10,15,20-tetraphenyl-21H,23H-porphine (TPP). OLEDs comprised of the TPP-containing emissive layer produce an emission spectrum comprised of two narrow bands that are centered at about 650 and about 713 nm, as shown in FIG. 1. The emission from this device involves fluorescence from the TPP dopant. One of the problems with the TPP-doped device is that the narrow band at 713 nm, which comprises about 40% of the emission, is not within a range that is useful for display applications. A second problem is that TPP-doped OLEDs are very unstable, such that the shelf life of such devices is typically very short. It would be desirable if these two aspects of TPP-doped devices could be improved. The present invention is directed to addressing these problems of prior art devices.

Another aspect of the present invention relates to the fact that, based on spin statistical arguments, it is generally understood that the majority of the excitons that are produced in an OLED are in a non-emissive triplet electronic state. Formation of such triplet states can result in a substantial loss of the excitation energy in the OLED via radiationless transitions to the ground state. It would be desirable if the total OLED quantum efficiency could be enhanced by utilizing this energy transfer pathway through the exciton triplet states, for example, by having the exciton triplet state energy transferred to an emissive material. Though it was known that the energy from an excited triplet state could be efficiently transferred under certain circumstances to the triplet state of a molecule that phosphoresces, prior to the disclosures contained in co-pending application having Ser. No. 08/980,986, now U.S. Pat. No. 6,303,238, which is incorporated herein in its entirety by reference, it had been thought that the phosphorescent decay rate would not be expected to be rapid enough to be adequate for use in a display device. U.S. Pat. No. 6,303,238 discloses that, in fact, practical OLEDs can be fabricated in which the emissive layer includes a phosphorescent compound. As a specific representative embodiment of such phosphorescent compounds, a platinum octaethylporphine (PtOEP) compound was disclosed having the chemical structure with the formula:

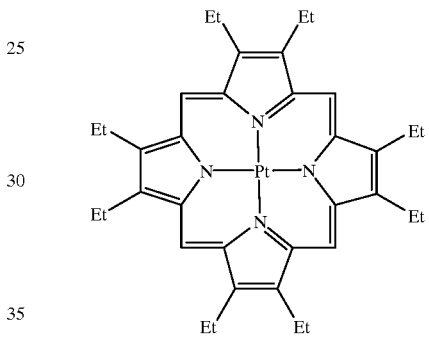

Whenever such compounds are doped, for example, into the $Alq_3$ layer of an OLED comprised of layers of ITO/TPD/$Alq_3$/Mg—Ag in sequence, the OLED was found to produce useful external quantum efficiencies with a very narrow emission having a half-width of about 30 mn centered at about 645 nm. Such a narrow band is of particular interest for use in OLEDs, since this band produces what is perceived to be a saturated red emission.

Though PtOEP may itself yet prove to have the most desirable combination of properties for use in OLEDs, such a compound has the disadvantage of producing the saturated red emission near the edge of the eye sensitivity curve, for which the standardized CIE photopic response function of the human eye is centered at about 550 nm. In particular, at the blue and red ends of the spectrum, there is a steep reduction in the eye sensitivity as a function of wavelength.

It would be desirable if phosphorescent compounds could be found which produce what is perceived to be a saturated red emission with a high external quantum efficiency, but with narrow peaks at somewhat shorter wavelengths for which there is a substantially higher eye sensitivity. For example, if the emission bandwidth could be kept substantially constant and the emission peak shifted about 20 nm toward shorter wavelengths, for an OLED producing the same number of photons, for example, an OLED with the same current and quantum yield, the perceived brightness of the device could be increased by a factor of about two. That is, though the number of photons coming from the two devices would be the same, the standard observer would perceive a factor of two increase in brightness for the device having the peak at the shorter wavelength. The emission would, however, be in a region that would still be perceived as saturated red and, thus, still be useful in an OLED.

The present invention is directed to materials and methods that may be used for fabricating OLEDs that address this objective.

ADVANTAGES AND SUMMARY OF THE INVENTION

The present invention is directed to OLEDs, and a method of fabricating OLEDs, in which emission from the device is obtained via a phosphorescent decay process wherein the phosphorescent decay rate is rapid enough to meet the requirements of a display device.

More specifically, the present invention is directed to OLEDs comprised of a material that is capable of receiving the energy from an exciton singlet or triplet state and emitting that energy as phosphorescent radiation.

One of the benefits of the present invention is that the phosphorescent decay process utilizes exciton triplet state energy that is typically wasted in an OLED via a radiationless energy transfer and relaxation process.

The present invention is further directed to materials and methods for fabricating OLEDs in which a phosphorescent dopant compound produces a highly saturated red emission in a spectral region for which the photopic response function for the human eye is significantly increased as compared with previously disclosed phosphorescent compounds.

In particular, the phosphorescent compounds of the present invention produce a highly saturated red emission with improved luminous efficacy as compared with OLEDs comprised of PtOEP, a compound that produces a narrow emission band that peaks at about 645 nm when the PtOEP is doped in an electron transporting layer comprised of tris-(8-hydroxyquinoline)-aluminum ($Alq_3$).

More specifically, the present invention is directed to a method of selecting phosphorescent dopant compounds for use in an OLED, wherein the phosphorescent compound is selected to be a platinum-porphine compound having reduced symmetry as compared with the 4-fold symmetry of compounds such as PtOEP, so as to obtain compounds having an emission peak shifted toward the peak of the eye sensitivity curve, while still remaining in a spectral region that is perceived as saturated red.

Further objectives and advantages of the present invention will be apparent to those skilled in the art from the detailed description of the disclosed invention.

DETAILED DESCRIPTION OF THE PREFERRED EMBODIMENTS

Figure 1:
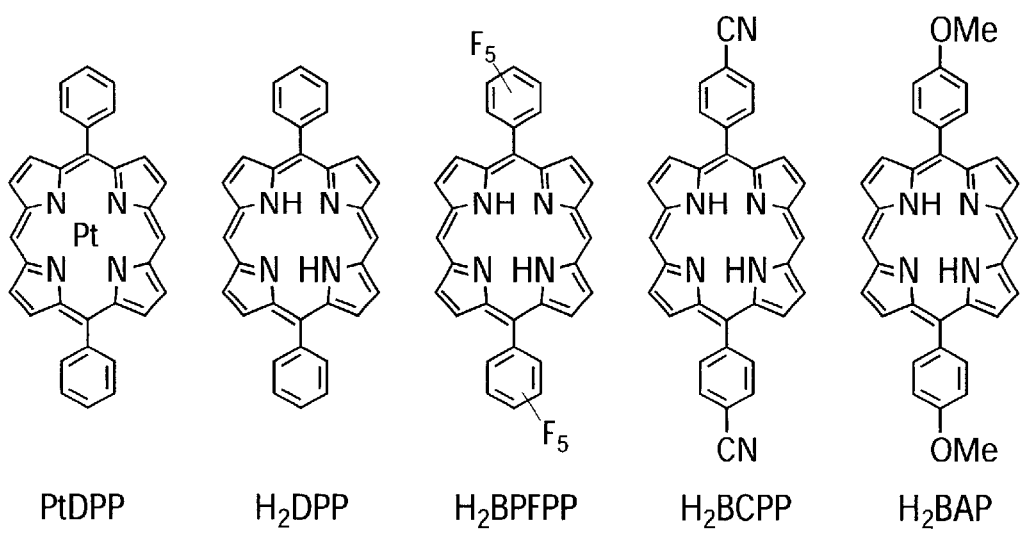
FIG. 1 shows a representative platinum porphyrin and four additional porphyrins that may be used to prepare platinum porphyrins for use as the platinum-substituted phosphorescent dopant compound in an OLED.

The present invention will now be described in detail for specific preferred embodiments of the invention, it being understood that these embodiments are intended only as illustrative examples and the invention is not to be limited thereto.

The present invention is directed to OLEDs in which emission from the device is obtained via a phosphorescent decay process wherein the phosphorescent decay rate is rapid enough to meet the requirements of a display device, and wherein, in particular, the phosphorescent dopant compound is comprised of a platinum porphyrin having reduced symmetry as compared, for example, with the 4-fold symmetry of PtOEP.

The advantage of selecting a phosphorescent dopant compound such as a platinum porphyrin compound as the emissive material of an OLED is based, inter alia, on two particular facts. First, the photoluminescent quantum yield for such compounds may be significantly greater than prior art compounds such as TPP. For example, PtOEP has a photoluminescent quantum yield of greater than 50%, and as high as 90% in the solid state, and TPP has a photoluminescent quantum yield of only about 10%. An improved photoluminescent quantum yield offers the possibility of fabricating OLEDs with increased efficiencies.

A second advantage that is offered by selecting a phosphorescent compound such as a platinum porphyrin compound is that the emission from such a compound typically comes from a triplet state. A molecule that is capable of being excited to a triplet state provides the possibility of having the energy transferred from the non-emissive exciton triplet state to a triplet state that is capable of radiatively emitting this energy as phosphorescent radiation. Though phosphorescence, which refers to radiation that comes from a triplet state, typically occurs at a much slower rate than fluorescence, which refers to radiation from a singlet state, the phosphorescence from a compound such as a platinum porphyrin compound may be sufficiently rapid to satisfy the requirements of certain display devices. In particular, a compound such as PtOEP, which has a lifetime of about 7 $\mu$sec when used as the dopant in an $Alq_3$ layer, may be used in passive matrix displays that require a switching time of not faster than about 10 $\mu$sec or in an active matrix display for which the switching time only needs to be about 10 msec.

A specific advantage of the present invention is that phosphorescent platinum porphyrin compounds are selected so as to have an emission peak shifted toward the peak of the eye sensitivity curve, while still remaining in a spectral region that is perceived as saturated red. In particular, by chemically modifying compounds such as PtOEP by breaking the 4-fold symmetry of the porphyrin ligand, it has been found that the emission peaks can be shifted about 15–30 nm towards shorter wavelengths, as compared with PtOEP.

The present invention is directed, in particular, to OLEDs containing a phosphorescent dopant compound having the structure with the formula:

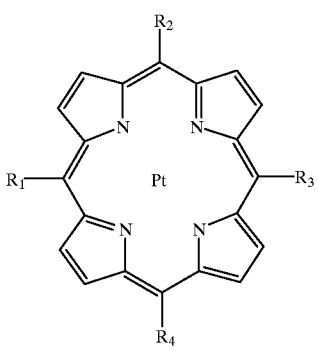

(II)

where the R-groups $R_1$, $R_2$, $R_3$ and $R_4$ are, independently of one another, alkyl, aryl or hydrogen, with the proviso that at least one of the R-groups is different from at least one other R-group.

Still more specifically, the OLEDs of the present invention are comprised of phosphorescent compounds having the structure with the formula:

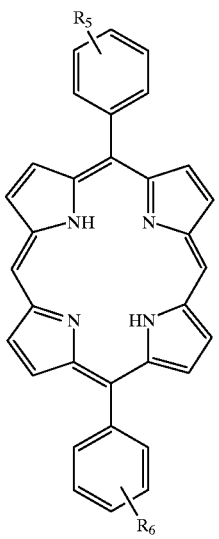

(III)

wherein $R_5$ and $R_6$ may be an electron donor or electron acceptor group, for example, —F, —CN or —$OCH_3$, and $R_5$ and $R_6$ may be the same or different.

As representative compounds to be used in OLEDS, the phosphorescent platinum compound may be selected by selectively substituting a phenyl-group at the 5,15 positions of the porphyrin ring so as to arrive at the platinum (II) 5,15-memo-diphenylporphyrin compound (PTDPP) as shown in FIG. 1. Alternatively, a platinum compound may be prepared from any one of the remaining 5,15-substituted porphyrin compounds that are also shown in FIG. 1. In particular, as representative embodiments of the present invention, the phosphorescent platinum porphyrin compound may be prepared from 5,15-memo-diphenylporphyrin ($H_2DPP$); 5,15-memo-bis(pentafluorophenyl)porphyrin ($H_2BPFPP$); 5,15-memo-bis(4-cyanophenyl)porphyrin ($H_2BCPP$); or 5,15-memo-bis(4-anisyl)porphyrin ($H_2BAP$). Such compounds may be prepared using methods such as described hereinafter.

Figure 2:
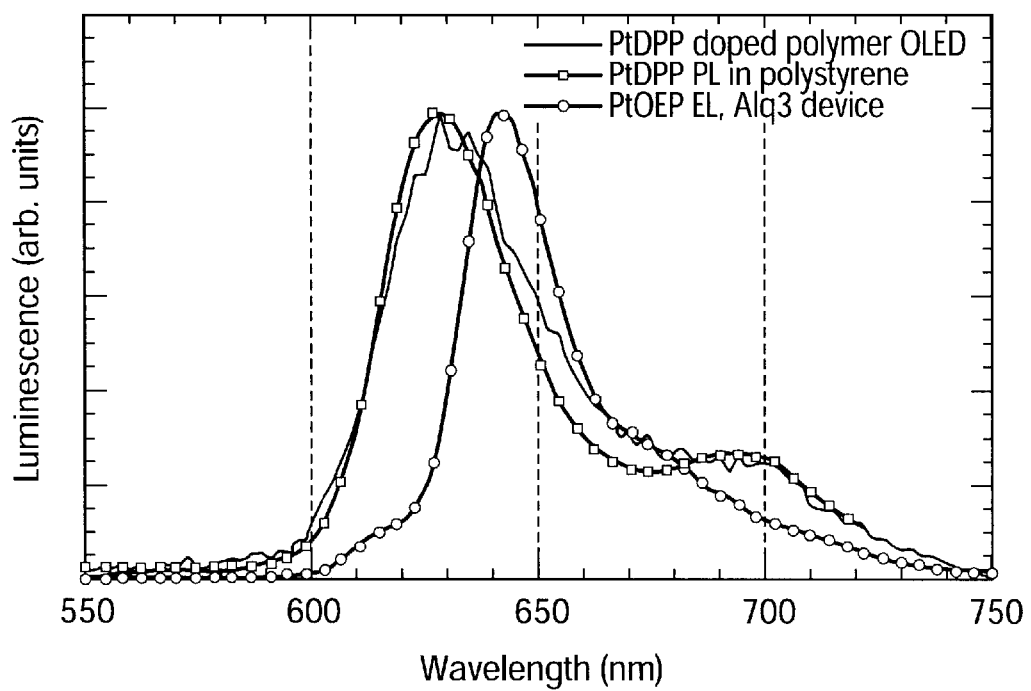
FIG. 2 shows the electroluminescent (EL) spectra of a PtDPP-doped polymer OLED as compared with the photoluminescent (PL) spectra of PtDDP in polystyrene and with the EL spectra of PtOEP doped in an $Alq_3$ device.

As a representative embodiment of the subject invention, OLEDs were fabricated in which PtDPP was doped as the phosphorescent platinum porphyrin compound. As shown in FIG. 2, the electroluminescent spectra of an OLED having PtDPP doped into a polymer mixture of polyvinyl carbazole (which is referred to as "PtDPP doped polymer OLED") produced an emission peak near the photoluminescence peak of PtDPP in polystyrene. These peaks were shifted about 20 nm towards lower wavelengths as compared with the electroluminescent spectra of an OLED having a PtDPP-doped $Alq_3$ layer.

Figure 3A:
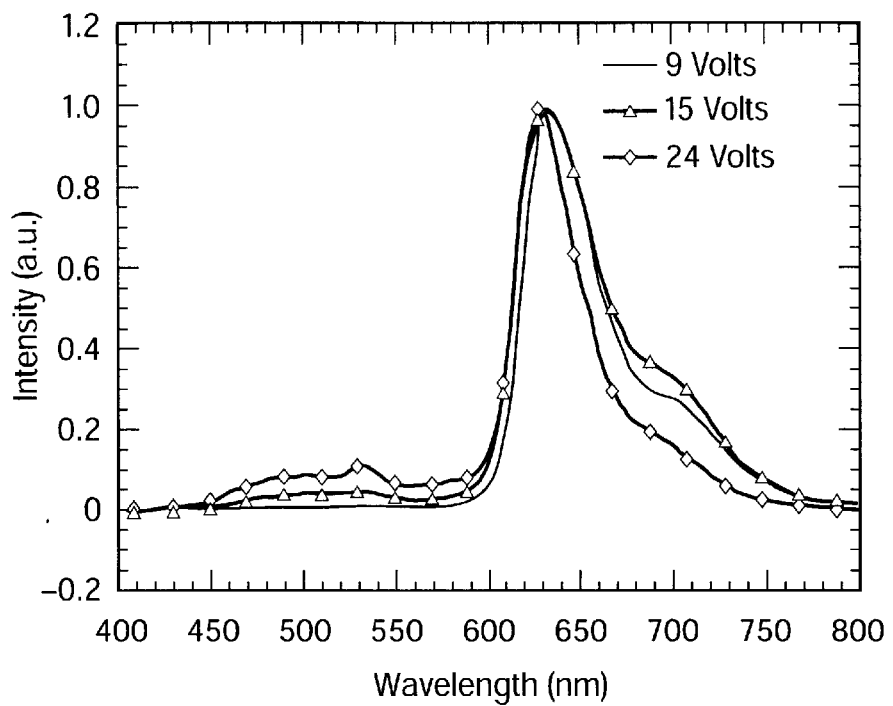
FIG. 3a shows the EL spectra as a function of applied voltage for PTDPP doped in the $Alq_3$ layer of an OLED comprised of ($ITO/NPD/Alq_3/MgAg$).
Figure 3B:
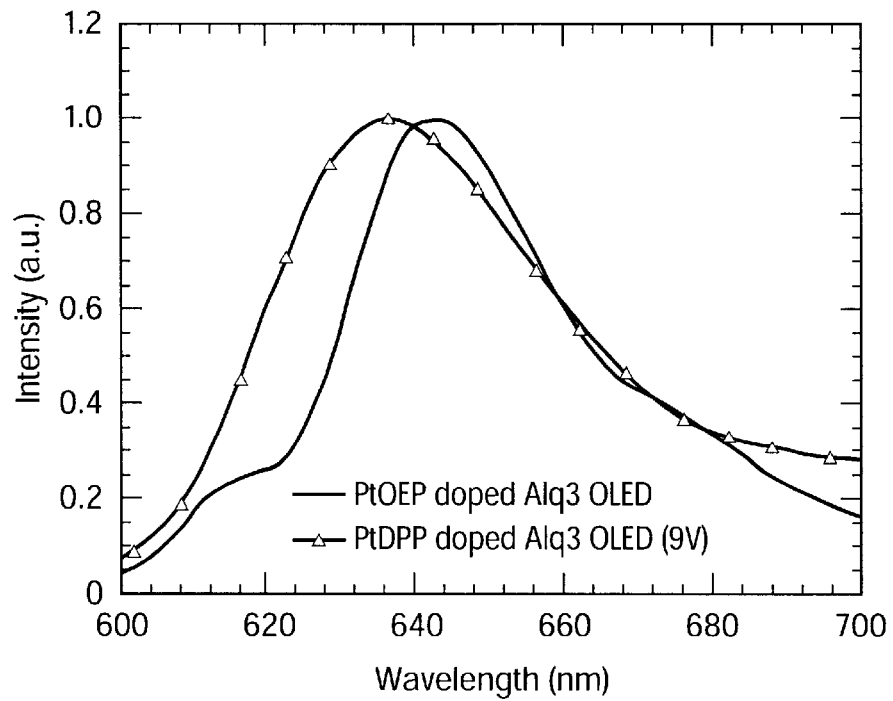
FIG. 3b shows the EL spectra of a PtDPP-doped $Alq_3$ OLED as compared with a PtOEP-doped $Alq_3$ OLED (with each device being operated at 9V).

As shown in FIG. 3a, for OLEDs comprised of layers of ITO/NPD/$Alq_3$-PtDPP/MgAg, (PtDPP being doped in the $Alq_3$ layer), an electroluminescent spectra is produced which has a narrow band of emission peaking at about 630 nm for OLEDs operated at 9V, 15V or 24V. The $Alq_3$-based device produced a small blue shift as the voltage was increased, apparently due to the increase in the $Alq_3$ emission in the spectra region from 500 to 550 nm. As shown in FIG. 3b, for an OLED having the $Alq_3$ layer doped with PtDPP, the emission peak was shifted about 15 nm towards shorter wavelengths as compared with the emission peak produced by an OLED having the $Alq_3$ layer doped with PtOEP. These results show that for OLEDs having equal quantum yields, an OLED having a PtDPP-doped $Alq_3$ layer would have 1.4 times the brightness of an OLED having a PtOEP-doped $Alq_3$ layer.

Figure 4:
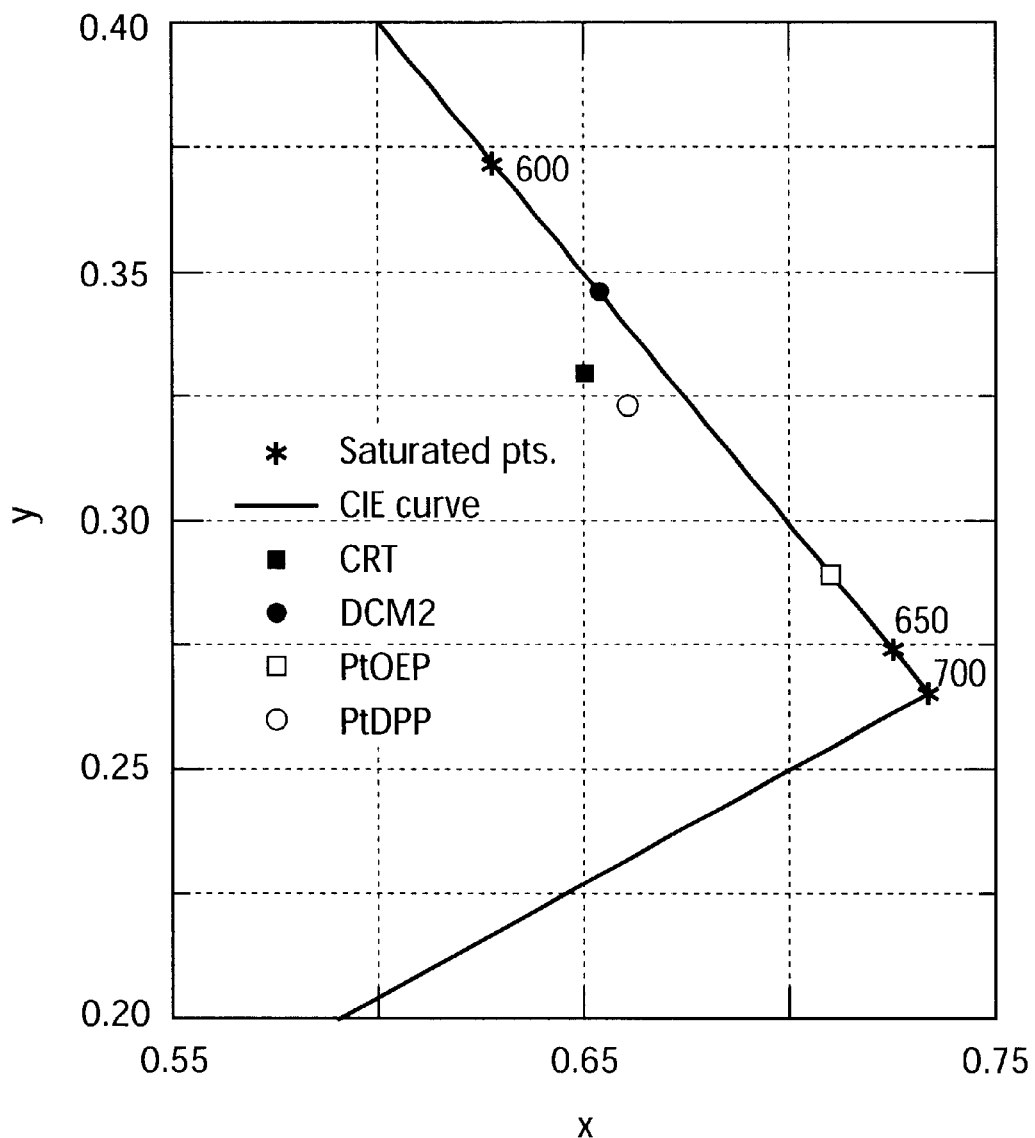
FIG. 4 shows the CIE coordinates and luminance outputs from a PtDPP-doped OLED as compared with other red-emitting OLEDs.

The practical significance of fabricating OLEDs having a 15–20 nm blue shift in the emission peak can be illustrated by the data as shown in the right hand corner of the CIE chromaticity diagram, which is shown in FIG. 4. Shown in this figure is the CIE chromaticity curve for which the (x, y) coordinates of saturated monochromatic lines at 600, 650 and 700 nm, respectively, are included. The (x, y) coordinates of the emission produced by an OLED having a PtDPP-doped $Alq_3$ layer is compared with OLEDs containing other red-emitting dopants, such as DCM2, indigo and PtOEP.

Figure 5:
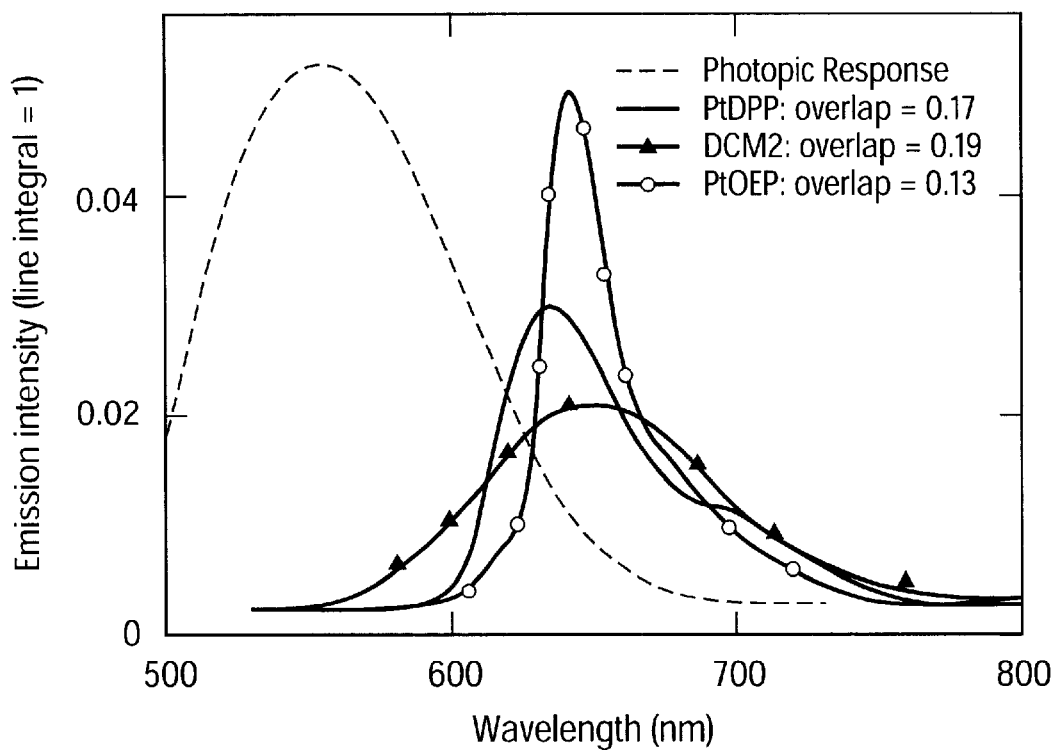
FIG. 5 shows the overlap of the CIE standardized photopic response curve for human eye sensitivity with the normalized emission spectra for compounds that produce a saturated red emission.

By using the CIE standardized photopic response curve for human eye sensitivity, which is shown as the broken line in FIG. 5, the relative brightness at a given photopic output level can be determined by calculating the overlap of the normalized emission spectra with the photopic response curve, as shown by the following equation, $$I_{lumens} \int (\text{photopic response})(EL\text{spectrum})d\lambda,$$

where $I_{lumens}$ is the perceived intensity in lumens. This function may be referred to as the luminous overlap integral. As illustrated by the representative data shown in FIG. 5, the luminous overlap integral of a PtDPP-emitting OLED, 0.17 (relative units), is significantly greater than that of a PtOEP-emitting OLED, 0.13. The net result is that for a PTDPP-emitting OLED, the CIE coordinates remain in the saturated red region of the chromaticity diagram, while the perceived brightness may be up to 40% or more greater than for a PtOEP-emitting OLED.

Though the luminous overlap integral of a DCM2-emitting OLED would be significantly higher than either PtDPP or PtOEP (0.19 vs. 0.17 or 0.13, respectively), that is, if the same photopic output levels could be realized, a DCM2-emitting OLED is not in fact nearly as bright, since the quantum efficiency of a DCM2-emitting OLED is substantially less than can be realized for OLEDs fabricated with the phosphorescent Pt-containing compounds.

DCM2, which has a structure represented by the formula:

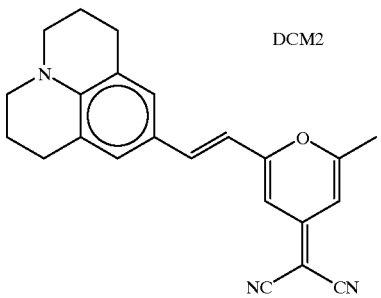

DCM2 has been described as a red emitting chromophore useful in OLED applications. C. W. Tang et al., *Electroluminescence of doped organic thin films*, *J. Appl. Phys.* 65, 3610 (1989).

The OLEDs of the present invention may be used, for example, in passive matrix flat panel displays having a switching time not faster than about 10 μsec, in active matrix displays for which the switching time only needs to be about 10 msec, or in low resolution display applications. In addition to selecting phosphorescent compounds according to their phosphorescent lifetimes, which for certain applications may mean selecting compounds having a phosphorescent lifetime not longer than about 10 μsec, the phosphorescent compounds may be selected according to their ability to effectively capture the exciton triplet energy from a charge carrier material and then to emit that excitation energy as phosphorescence in a narrow emission band corresponding to a highly saturated color, such as demonstrated by PtDPP in an $Alq_3$-based OLED.

A dopant capable of shifting the emission wavelength of an emissive layer comprised only of a host compound is added to the host compound in an amount effective to shift the wavelength of emission so that the LED device preferably emits light that is perceived by the human eye to be close to one of the primary colors. Although it is recognized that characterization of color perception is a subjective exercise, a quantitative chromaticity scale has been developed by the Commission Internationale de l'Eclairage (International Commission of Illumination), otherwise known as the CIE standard. According to this standard, a saturated color may be represented by a single point, with specific quantitative coordinates according to the defined axes of the chromaticity scale. It will be appreciated by one of skill in the art that such a single point on the CIE scale would represent a standard or a goal that, in practical terms, is difficult, but fortunately, unnecessary, to attain.

In the preferred embodiments of the present invention in which the OLED predominantly produces a primary color, the dopant is incorporated into a host compound so that the OLED emits light that is perceived by the human eye to be close to a saturated primary color. Through the practice of the present invention, it is intended that OLEDs be constructed which can be characterized by an emission that is close to an absolute (or saturated) chromaticity value, as that would be defined by the CIE scale. Furthermore, LED's utilizing the materials of the present invention are also intended to be capable of a display brightness that can be in excess of 100 $cd/m^2$ although somewhat lower values, perhaps as low as 10 $cd/m^2$, may be acceptable in certain cases.

The host compounds as defined herein are compounds which can be doped with dopants that emit light with the desired spectral characteristics. Such compounds include, but are not limited to, the emitting compounds and host compounds as described in U.S. patent application Ser. No. 08/693,359, filed Aug. 6, 1996, incorporated herein in its entirety by reference. The term "host" is used to refer to the compound in the emissive layer that functions as the component, that is, "receiving compound" which receives the hole/electron recombination energy and then by an emission/absorption energy transfer process, transfers that excitation energy to the dopant compound, which is typically present in much lower concentrations. The dopant may then relax to an excited state having a slightly lower energy level, which preferentially radiates all of its energy as luminescent emission in a desired spectral region. A dopant that radiates 100% of the dopant's excited state excitation energy is said to have a quantum efficiency of 100%. For host/dopant concentrations which are to be used in a color tunable SOLED, preferably most, if not all, of the host's excitation energy is transferred to the dopant which in turn radiates, perhaps from a lower energy level, but with a high quantum efficiency, to produce visible radiation having a desired chromaticity. The present invention is directed toward phosphorescent compounds that are intended to serve as dopants which satisfy these demanding energy transfer requirements.

As the term host compound is used herein, it will be appreciated that such compounds can be found in an electron transporting/emissive layer or a hole transporting/emissive layer of a single heterostructure OLED device or in the separate emissive layer of a double heterostructure device. As will be recognized by one of skill in the art, use of the dopant species such as disclosed herein makes it possible to extend not only the range of colors emitted by the OLED, but also to extend the range of possible candidate species for host and/or dopant compounds. Accordingly, for effective host/dopant systems, although the host compound can have a strong emission in a region of the spectrum where the dopant species strongly absorbs light, the host species preferably does not have an emission band in a region where the dopant also emits strongly. In structures where the host compound also functions as a charge carrier, then additional criteria such as redox potential for the species also becomes a consideration. In general, however, the spectral characteristics of the host and dopant species are the most important criteria.

The amount of dopant that is present is that amount which is sufficient to shift the emission wavelength of the host material as close as possible to a saturated primary color, as that would be defined according to the CIE scale. Typically, the effective amount is from about 0.01 to 10.0 mol %, based on the emitting layer. The primary criterion for determining an appropriate doping level is the level which is effective for achieving an emission with the appropriate spectral characteristics. By way of example, and without limitation, if the amount of dopant species is at too low a level, then emission from the device will also comprise a component of light from the host compound itself, which will be at shorter wavelengths than the desired emission form the dopant species. In contrast, if the level of dopant is too high, emission efficiencies could be adversely affected by self-quenching, a net non-emissive mechanism. Alternatively, too high levels of the dopant species could also adversely affect the hole or electron transporting properties of the host material.

The OLEDs of the present invention are comprised of a heterostructure for producing electroluminescence which may be fabricated as a single heterostructure or as a double heterostructure. The materials, methods and apparatus for preparing the organic thin films of a single or double heterostructure are disclosed, for example, in U.S. Pat. Nos. 5,554,220, 5,703,436 and 5,707,745, which are incorporated herein in their entirety by reference. As used herein, the term "heterostructure for producing electroluminescence" refers to a heterostructure that includes, for a single heterostructure, in sequence, a hole injecting anode layer, a hole transporting layer, an electron transporting layer, and a cathode layer. An additional layer or layers may be present between one or more of the sequential pairs of these layers. For example, for a double heterostructure, a separate emissive layer is included between the hole transporting layer and the electron transporting layer. This separate emissive layer may be characterized as being a "thin luminescent layer." Alternatively, or in addition, a hole injection enhancement layer may be present between the anode layer and the hole transporting layer and/or an electron injecting and interface layer may be present between the cathode layer and the electron transporting layer.

Either the anode layer or the cathode layer may be in contact with a substrate and each electrode is connected to electrical contacts which are capable of delivering a voltage across the device causing it to produce electroluminescence from an electron transporting layer, a hole transporting layer or a separate emissive layer. If the cathode layer is deposited on the substrate, the device may be referred to as having an inverted OLED (IOLED) structure. An inverted structure may also be referred to as an "OILED" structure. If the heterostructure for producing electroluminescence is included as part of a stacked OLED (SOLED), one or both of the electrodes of an individual heterostructure may be in contact with an electrode of an adjacent heterostructure. Alternatively, dependent on the circuitry used to drive the SOLED, an insulating layer may be provided between the adjacent electrodes of the OLEDs in the stack.

The single or double heterostructures as referred to herein are intended solely as examples for showing how an OLED embodying the present invention may be fabricated without in any way intending the invention to be limited to the particular materials or sequence for making the layers shown. For example, a single heterostructure typically includes a substrate which may be opaque or transparent, rigid or flexible, and/or plastic, metal or glass; a first electrode, which is typically a high work function, hole-injecting anode layer, for example, an indium tin oxide (ITO) anode layer; a hole transporting layer; an electron transporting layer; and a second electrode layer, for example, a low work function, electron-injecting, metal cathode layer of a magnesium-silver alloy, (Mg:Ag) or of a lithium-aluminum alloy, (Li:Al). Alternatively, as disclosed in U.S. Ser. Nos. 08/964,863 and 09/054,707, which are incorporated in their entirety by reference, the cathode may be a non-metallic material such a ITO, the term "non-metallic" being used to embrace still other transparent conducting inorganic layers, as well as materials comprised of metals that may be present as one of the elements in a chemical compound, for example, as an oxide. However, the term "non-metallic" does not embrace materials comprised predominantly of the free metal nor does the term embrace metal alloys.

Materials that may be used as the substrate in a representative embodiment of the present invention include, in particular, glass, transparent polymer such as polyester, sapphire or quartz, or substantially any other material that may be used as the substrate of an OLED.

Materials that may be used as the hole-injecting anode layer in a representative embodiment of the present invention include, in particular, ITO, Zn—In—$SnO_2$ or $SbO_2$, or substantially any other material that may be used as the hole-injecting anode layer of an OLED.

Materials that may be used in the hole transporting layer in a representative embodiment of the present invention include, in particular, N,N'-diphenyl-N,N'-bis(3-methylpheny)1-1'biphenyl-4,4'diamine (TPD), 4,4'-bis[N-(1-naphthyl)-N-phenyl-amino]biphenyl ($\alpha$-NPD) or 4,4'-bis[N-(2-naphthyl)-N-phenyl-amino]biphenyl ($\beta$-NPD).

Materials that may be used as the electron transporting layer include, in particular, tris-(8-hydroxyquinoline)-aluminum ($Alq_3$) and carbazole-substituted compounds.

Materials that may be used as the separate emissive layer, if present, include, in particular, dye-doped $Alq_3$, or substantially any other material that may be used as the separate emissive layer of an OLED.

The insulating layer, if present, may be comprised of an insulating material such as $SiO_2$, $SiN_x$ or $AlO_2$, or substantially any other material that may be used as the insulating material of an OLED, which may be deposited by a variety of processes such as plasma enhanced chemical vapor deposition (PECVD), electron beam, etc.

The hole injecting enhancement layer may in some cases be comprised of the same material, CuPc, as is used in the electron injecting and interface layer. In each case, the CuPc layer may be in direct contact with an ITO electrode, with the distinction between the two CuPc layers being that in one case the CuPc layer is in contact with an ITO layer that functions as an anode and in the other case the ITO layer functions as a cathode. In each case, the CuPc layer functions as a charge carrier and interface layer. On the one hand when in contact with the ITO anode, the CuPc layer assists in injecting and transporting holes from the anode to a hole transporting layer, and on the other hand when in contact with the ITO cathode, the CuPc layer assists in injecting and transporting electrons from the cathode to an electron transporting layer. The term "electron injecting interface layer" is used to refer to this layer that is present between and in contact with the cathode layer and the electron transporting layer of the heterostructure. The CuPc layer, in each case, may also function as a protection layer that protects any underlying organic layers, if present, from damage during the ITO deposition process. The protection layer may also be comprised of others materials such a 3,4,9,10-perylenetetra-carboxylic dianhydride (PTCDA). Whenever the ITO layer is present as the electrode in a SOLED structure, opposite faces of the ITO may function as an anode and cathode, respectively.

The OLEDs of the present invention have the advantage that they can be fabricated entirely from vacuum-deposited molecular organic materials as distinct, for example, from OLEDs in which some of the layers are comprised of polymeric materials, which cannot be readily deposited using vacuum deposition techniques. A vacuum-deposited material is one which can be deposited in a vacuum typically having a background pressure less than one atmosphere, preferably about $10^{-5}$ to about $10^{-11}$ torr for vacuum deposition, or about 50 torr to about $10^{-5}$ torr for vapor deposition.

Although not limited to the thickness ranges recited herein, the substrate may be as thin as $10\mu$, if present as a flexible plastic or metal foil substrate, such as aluminum foil, or substantially thicker if present as a rigid, transparent or opaque, substrate or if the substrate is comprised of a silicon-based display driver; the ITO anode layer may be from about 500 Å (1 Å=$10^{-8}$ cm) to greater than about 4000 Å thick; the hole transporting layer from about 50 Å to greater than about 1000 Å thick; the separate emissive layer of a double heterostructure, if present, from about 50 Å to about 200 Å thick; the electron transporting layer from about 50 Å to about 1000 Å thick; and the metal cathode layer from about 50 Å to greater than about 100 Å thick, or substantially thicker if the cathode layer includes a protective silver layer and is opaque.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED is comprised of a heterostructure for producing electroluminescence wherein the heterostructure is comprised of an emissive layer containing a phosphorescent compound.

The materials that may be used as the substrate, the hole-injecting anode layer, the hole transporting layer, the electron transporting layer, the electron-injecting, metal cathode layer or the electron-injecting, non-metallic cathode layer, the protection layer, if present, the separate emissive layer, if present, or the insulating layer, if present, include the materials as disclosed in these co-pending applications.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

This invention will now be described in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

AN EXAMPLE OF THE INVENTION

The procedures that were used for fabrication of Organic Light-Emitting Devices (OLEDs) were as follows:

The hole transporting material TPD and the electron transporting material $Alq_3$ were synthesized according to literature procedures, and were sublimed before use. The dopant PtDPP compound and additional porphyrin compounds that may also be platinated were synthesized as described below.

OLEDs were Prepared Using the Following Procedures

The ITO/Borosilicate substrates (100Ω/square) were cleaned by sonicating with detergent for five minutes followed by rinsing with deionized water. They were then treated twice in boiling 1,1,1-trichloroethane for two minutes. The substrates were then sonicated twice with acetone for two minutes and twice with methanol for two minutes.

The background pressure prior to deposition was normally $7 \times 10^{-7}$ torr or lower and the pressure during the deposition was around $5 \times 10^{-7}$ to $1.1 \times 10^{-6}$ torr.

All the chemicals were resistively heated in various tantalum boats. TPD was first deposited at a rate from one to four Å/s. The thickness was typically controlled at 300 Å.

The electron transporting layer $Alq_3$ was doped with the dopant compound, for example, PtDPP. Typically, the dopant was first vaporized with the substrates covered. After the rate of the dopant was stabilized, the host material was vaporized to at a certain rate. The cover over the substrates was then opened and the host and guest were deposited at the desired concentration. The rate of dopant was normally 0.1–0.2 Å/s. The total thickness of this layer was controlled at about 450 Å.

The substrates were removed from the deposition system and masks were put directly on the substrates. The masks were made of stainless steel sheet and contain holes with diameters of 0.25, 0.5, 0.75 and 1.0 mm. The substrates were then put back into vacuum for further coating.

Magnesium and silver were co-deposited at a rate normally of 2.6 Å/s. The ratio of Mg:Ag varied from 7:1 to 12:1. The thickness of this layer was typically 500 Å. Finally, 1000 Å Ag was deposited at the rate between one to four Å/s.

The devices were characterized within five hours of fabrication. Typically electroluminescent spectra, I–V curves, and quantum yields were measured from direct front.
Syntheses of Compounds and Their Characterization 2,2'-Dipyrrylmethane was prepared from a modified literature procedure (*Aust. J. Chem.,* 1969, 22, 229–249):

2,2'-Dipyrrylthione. To a vigorously stirred solution of 7.0 mL (90 mmol) of thiophosgene in 150 mL of dry THF at 0° C. was added dropwise 12.5 g (186 mmol) of pyrrole. After 30 minutes, methanol (20 mL) was added and the mixture was further stirred for 30 minutes at room temperature. The resulting mixture was then evaporated to dryness. This crude material was used for the next step without further purification.

2,2'-Dipyrrylketone. To the aforementioned crude thione in 200 mL of 95% EtOH containing 10 g of KOH was added 17 mL of $H_2O_2$ (30%) at 0° C. slowly. The mixture was stirred at 0° C. for 2 hours and then at 60° C. for 30 minutes after which was concentrated to ⅕ of its original volume. 100 mL of $H_2O$ was added and the precipitate was filtered, washed with cold EtOH and dried to give the product (5.6 g, 39% from thiophosgene) which was sufficiently pure for the next step.

2,2'-Dipyrrylmethane. To a solution of 3.3 g (20.1 mmol) of 2,2'-dipyrrylketone in 200 mL of 95% ethanol containing 3.3 mL of morpholine under $N_2$ at reflux was added $NaBH_4$ (1.7 g×6) in several portions. 3 mL of $H_2O$ was added 10 minutes after each addition. The mixture was further refluxed for 2 hours after the last addition. 300 mL of $H_2O$ was then added and the mixture was extracted several times with $Et_2O$. The combined extract was dried with $MgSO_4$ and concentrated to give a thick oil which was extracted with hexane until the extract showed no appreciable amount of the product by TLC. The combined hexane portions were concentrated to give 2.3 g (78%) of pale yellow crystals as the product.
General Synthesis of 5,15-meso-diphenylporphyrins 2,2'-Dipyrrylmethane (0.5 g, 3.42 mmol) and an equimolar amount of the aldehyde were dissolved in 500 mL of dry $CH_2Cl_2$. The solution was purged with $N_2$ for 15 minutes. Trifluoroacetic acid (154 μL, 2.6 mmol) was then added via syringe and the mixture was stirred for 3 hours under $N_2$ in the absence of light. 2,3-Dichloro-5,6-dicyanoquinone (1.04 g, 4.6 mmol) was added and stirring was continued for 30 minutes. The resulting dark solution was concentrated to ⅓ of its original volume and poured onto a column of silica gel packed with hexane. Elution with $CH_2Cl_2$ afforded a purple band which was concentrated to give purple solids that were filtered and washed with ethanol followed by heaxane. The solids were pure enough for photoluminescence measurements.

5,15-memo-diphenylporphyrin ($H_2$DPP): yield: 0.63 g., 80%, MS (EI) m/z (relative intensity) 462 ($M^+$, 100), 386 (50), 368 (30), 313 (25), 231 (50).

5,15-memo-bis(pentafluorophenyl)porphyrin ($H_2$BPFPP): yield: 0.05 g, 5%, MS (EI), m/z (relative intensity) 642 ($M^+$, 100), 623 (8), 602 (8), 368 (45), 321 (35), 236 (40).

5,15-memo-bis(4-cyanophenyl)porphyrin (H$_2$BCPP): yield: 0.09 g, 10%, MS (EI), m/z (relative intensity) 512 (M$^+$, 100), 411 (50), 368 (35), 355 (40), 294 (45), 281 (50).

5,15-memo-bis(4-anisyl)porphyrin (H$_2$BAP): yield: 0.09 g, 10%, MS (EI) m/z (relative intensity) 522 (M$^+$, 8), 416 (100), 401 (20), 372 (23).

Platinum (II) 5,15-memo-diphenylporphyrin (PtDPP). A mixture of H$_2$DPP (0.05 g, 0.11 mmol) and Pt(PhCN)$_2$Cl$_2$ (0.1 g, 0.22 mnol) in 10 mL of dry toluene was refluxed for 24 hours under N$_2$. The resulting solution was dried completely under vacuum to remove traces of PhCN. The dark solid was dissolved in CH$_2$Cl$_2$ and chromatographed using hexane: CH$_2$Cl$_2$ (1:1, v/v) as the eluent to give red solids as the product (0.04 g, 56%).

$^1$H NMR: δ10.15 (s,2H), 9.207 (dd, 4H, J$_1$=12 Hz, J$_2$=7.5 Hz), 8.93 (dd, 4H, J$_1$=12 Hz, J$_2$=7.5 Hz), 8.18 (m, 4H), 7.77 (m, 6H). %, MS (EI) m/z (relative intensity) 655 (M$^+$, 100), 577 (30), 326 (50), 288 (35).

What is claimed is:

1. An organic light emitting device comprising a heterostructure for producing electroluminescence wherein the heterostructure is comprised of an emissive layer, and the emissive layer comprises a host material containing a phosphorescent dopant compound having the structure with formula (II):

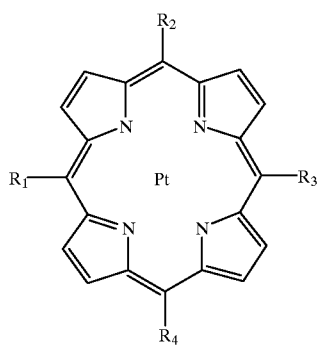

(II)

wherein R$_1$ and R$_3$ are hydrogen and R$_2$ and R$_4$ are unsubstituted phenyl groups.

2. The organic light emitting device of claim 1 wherein the emissive layer is an electron transporting layer.

3. The organic light emitting device of claim 1 wherein the emissive layer is a hole transporting layer.

4. The organic light emitting device of claim 3 wherein the hole transporting layer is comprised of N,N'-diphenyl-N,N'-bis(3-methylpheny)1-1'biphenyl-4,4'diamine.

5. The organic light emitting device of claim 1 wherein the phosphorescent dopant compound has a phosphorescent lifetime not longer than about 10 µsec.

6. The organic light emitting device of claim 1 wherein the emissive layer is an electron transporting layer comprised of tris-(8-hydroxyquinoline)-aluminum.

7. The organic light emitting device of claim 6 wherein the heterostructure for producing luminescence is comprised of a hole transporting layer comprised of N,N'-diphenyl-N,N'-bis(3-methylpheny)1-1'biphenyl-4,4'diamine.

8. The organic light emitting device of claim 1 wherein the heterostructure for producing electroluminescence is comprised of, in sequence, a substrate, a cathode layer, an electron transporting layer, a hole transporting layer and an anode layer.

9. The organic light emitting device of claim 1 wherein the heterostructure for producing electroluminescence is comprised of, in sequence, a substrate, an anode layer, a hole transporting layer, an electron transporting layer, and a cathode layer.

10. A display incorporating the organic light emitting device of claim 1.

11. A vehicle incorporating the organic light emitting device of claim 1.

12. A computer incorporating the organic light emitting device of claim 1.

13. A television incorporating the organic light emitting device of claim 1.

14. A printer incorporating the organic light emitting device of claim 1.

15. A wall, theater or stadium screen incorporating the organic light emitting device of claim 1.

16. A billboard or a sign incorporating the organic light emitting device of claim 1.

17. A stacked organic light emitting device comprising a
 a first heterostructure for producing electroluminescence and
 a second heterostructure for producing electroluminescence, the second heterostructure being stacked on the first heterostructure;
 wherein at least one of the heterostructures is comprised of an emissive layer, and the emissive layer comprises a host material containing a phosphorescent dopant compound having the structure with formula (II):

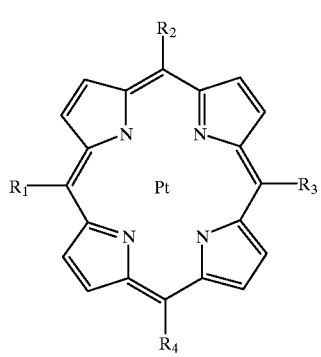

(II)

wherein R$_1$ and R$_3$ are hydrogen and R$_2$ and R$_4$ are unsubstituted phenyl groups.

18. A method of fabricating an organic light emitting device comprising:
 preparing a heterostructure for producing electroluminescence, wherein the preparation process includes the step of forming an emissive layer, and the emissive layer comprises a host material containing a phosphorescent dopant compound having the structure with formula (II):

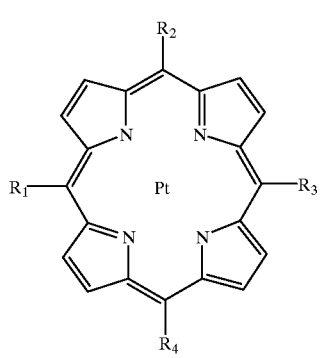

(II)

wherein R$_1$ and R$_3$ are hydrogen and R$_2$ and R$_4$ are unsubstituted phenyl groups.

* * * * *